United States Patent [19]

Rendenbach-Mueller et al.

[11] Patent Number: 5,414,006

[45] Date of Patent: May 9, 1995

[54] ARYLALKOXYTHIOCOUMARINS, THE PREPARATION THEREOF AND THERAPEUTIC COMPOSITIONS CONTAINING THESE

[75] Inventors: Beatrice Rendenbach-Mueller, Waldsee; Ulrich Karl; Harald Weifenbach, both of Ludwigshafen, all of Germany

[73] Assignee: BASF Aktiengesellschaft, Ludwigshafen, Germany

[21] Appl. No.: 136,033

[22] Filed: Oct. 14, 1993

[30] Foreign Application Priority Data

Oct. 22, 1992 [DE] Germany ............... 42 35 603.2

[51] Int. Cl.$^6$ .................. C07D 417/12; A01K 31/37
[52] U.S. Cl. ..................... 514/363; 514/364; 514/365; 514/378; 514/406; 514/444; 514/457; 548/136; 548/143; 548/204; 548/247; 548/364.4; 549/60; 549/289
[58] Field of Search ............... 549/60, 289; 548/204, 548/247, 364.4, 136, 143; 514/363, 364, 365, 378, 406, 444, 451

[56] References Cited

U.S. PATENT DOCUMENTS 5,073,563  12/1991  Frickel et al. .
5,100,914  3/1992   Rendenbach-Mueller et al. .

FOREIGN PATENT DOCUMENTS 0363793  4/1990  European Pat. Off. .
0363796  4/1990  European Pat. Off. .

OTHER PUBLICATIONS

Martix Advanced Org. Chem 3rd ed p. 794 (1985).

*Primary Examiner*—Robert Gerstl
*Attorney, Agent, or Firm*—Oblon, Spivak, McClelland, Maier, & Neustadt

[57] ABSTRACT

Arylalkoxythiocoumarins of the formula where
  $R^1$ and $R^2$ are each, independently of one another, hydrogen, $C_1$–$C_5$-alkyl, trifluoromethyl, phenyl or halogen, or together are a $C_3$–$C_5$-alkylene chain, and
  X is oxygen or sulfur,
  $R^3$ is $C_1$–$C_5$-alkyl or halogen,
  n is an integer from 0 to 3,
  $R^4$ is hydrogen or $C_1$–$C_4$-alkyl and
  Ar is phenyl, which can be mono- or disubstituted by halogen, $C_1$–$C_6$-alkyl, $C_3$–$C_7$-cycloalkyl, $C_1$–$C_6$-alkoxy, nitro, cyano, trifluoromethyl or a combination of these substituents or is a heteroaromatic ring which has from one to three heteroatoms which can, independently of one another, be N, O or S, and which can be substituted by $C_1$–$C_6$-alkyl, $C_3$–$C_7$-cycloalkyl, $C_1$–$C_6$-alkoxy, $C_1$–$C_4$-alkoxy-substituted $C_1$–$C_6$-alkyl, 5–6-membered oxacycloalkyl, benzyl, $C_1$–$C_5$-alkoxycarbonyl, perfluoro-$C_1$–$C_2$-alkyl, phenyl or halogen, are prepared as described and used in therapeutic compositions, especially for treating disorders of the central nervous system.

4 Claims, No Drawings

ARYLALKOXYTHIOCOUMARINS, THE PREPARATION THEREOF AND THERAPEUTIC COMPOSITIONS CONTAINING THESE

The present invention relates to novel phenyl- and heterarylalkoxythiocoumarins of the formula I, to the preparation thereof and to therapeutic compositions which contain these compounds as active ingredients, especially for treating disorders of the central nervous system.

It is an object of the present invention to develop novel therapeutic compositions, especially for treating disorders of the central nervous system.

We have found that this object is achieved by the novel compounds of the formula I as claimed in claim 1, the preparation process as claimed in claim 2 and the therapeutic compositions as claimed in claims 3 and 4.

In the formula I

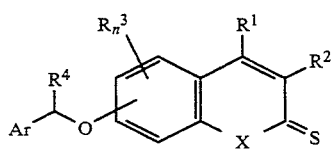
I $R^1$ and $R^2$, which can be identical or different, are each hydrogen, $C_1$–$C_5$-alkyl, $CF_3$, phenyl or halogen, and $R^1$ and $R^2$ can together form a chain of 3–5 carbons, X is oxygen or sulfur, $R^3$ is $C_1$–$C_5$-alkyl or halogen, n is an integer from 0 to 3, $R^4$ is hydrogen or $C_1$–$C_4$-alkyl and Ar is phenyl, which can be mono- or disubstituted by halogen, $C_1$–$C_6$-alkyl, $C_3$–$C_7$-cycloalkyl, $C_1$–$C_6$-alkoxy, nitro, cyano, trifluoromethyl or a combination of these substituents or is a heteraromatic ring which has from one to three heteroatoms which can, independently of one another, be N, O or S, and which can be substituted by $C_1$–$C_6$-alkyl, $C_3$–$C_7$-cycloalkyl, $C_1$–$C_6$-alkoxy, $C_1$–$C_4$-alkoxy-substituted $C_1$–$C_6$-alkyl, 5- 6-membered oxacycloalkyl, benzyl, $C_1$–$C_5$-alkoxycarbonyl, perfluoro-$C_1$–$C_2$-alkyl, phenyl or halogen.

Halogen is preferably fluorine, chlorine or bromine.

The compounds of the formula I can be prepared, for example, by converting the appropriate coumarin derivatives of the formula II

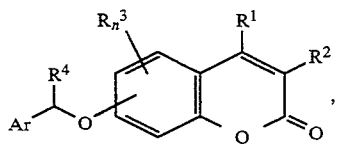
II where $R^1$, $R^2$, $R^3$, $R^4$, n and Ar have the abovementioned meanings, with a thiolating reagent into the sulfur compounds.

Examples of suitable thiolating reagents are sulfur, hydrogen sulfide and its alkali metal and ammonium salts, Lawesson's reagent (Lawesson, S. O., Org. Synth. 62, (1984) 158–164), Belleau's reagent (Lajoie, G.; Lépine, F.; Maziak L.; Belleau, B., Tetrahedron Lett. 24, (1983) 3815–3818), phosphorus pentasulfide or reagents prepared in situ from phosphorus pentasulfide by addition of pyridine, triethylamine, sodium or potassium bicarbonate or sodium or potassium carbonate.

The reactions can be carried out, for example, by mixing the coumarins II with the thiolating reagent, preferably in a solvent.

Suitable solvents depend on the chosen thiolating reagent and are benzene or toluene, methylene chloride, chloroform, acetonitrile, tetrahydrofuran, hexamethylphosphoric triamide, pyridine, ethanol or acetic acid. The reactions are expediently carried out at from room temperature to the boiling point of the solvent.

The products are isolated and purified by conventional methods, for example by recrystallization from a solvent, by column chromatography, extraction or, where appropriate, conversion into an acid addition compound if Ar has basic characteristics.

The compounds of the formula II can be prepared, for example, by reacting a hydroxycoumarin of the formula III

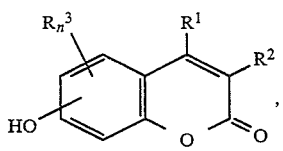
III where $R^1$, $R^2$, $R^3$ and n have the abovementioned meanings, in a conventional manner with a compound of the formula IV

IV where $R^4$ and Ar are as defined above, and Y is a nucleofugic leaving group such as chlorine, bromine or $R^5SO_2O$. $R^5$ is lower alkyl or phenyl which is unsubstituted or substituted by $C_1$–$C_3$-alkyl or halogen. The reaction can be carried out as described, for example, in Houben-Weyl, Georg Thieme-Verlag, Stuttgart 1965, Vol. 6/3, pages 54 et seq., by heating the two components, preferably in the presence of an inert solvent such as benzene, toluene, methylene chloride, acetone, a lower alcohol, dimethylformamide or water. The reactions are expediently carried out at from room temperature to the boiling point of the solvent. The liberated acid is generally trapped by adding bases such as alkali metal or alkaline earth metal hydroxides or carbonates or a mines such as pyridine or triethylamine. In place of the hydroxycoumarins of the formula III, it is also possible to react their alkali metal salts with the compounds of the formula IV, preferably under anhydrous conditions in aprotic solvents such as ether, tetrahydrofuran, dimethylformamide, dimethoxyethane or dimethyl sulfoxide. Bases which can be used in these cases are alkali metal hydrides or alcoholates. The products are isolated and purified by conventional methods, for example by recrystallization from a solvent, by column chromatography, extraction or, where appropriate, conversion into an acid addition compound if Ar has basic characteristics.

The hydroxycoumarins III can be prepared by known methods as are described, for example, in Elderfield R. C., Heterocyclic compounds, John Wiley-Verlag, New York 1951, Vol. 2, pages 174 et seq., for example by condensing dihydroxybenzenes of the formula V

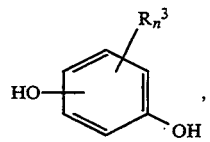

where $R^3$ and n have the abovementioned meanings, with β-keto carboxylic esters of the formula VI

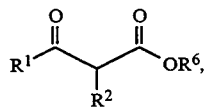

where $R^1$ and $R^2$ have the abovementioned meanings, and $R^6$ is $C_1$–$C_6$-alkyl, in the presence of a condensing agent such as sulfuric acid, phosphorus pentoxide or aluminum chloride.

The compounds of the formula IV are either known and commercially available in some cases, or can be prepared by conventional chemical processes. Methods for synthesizing thiophene derivatives are to be found, for example, in: Comprehensive Heterocyclic Chemistry, A. R. Katritzky and C. W. Rees, Vol. 4, pages 863 et seq., Pergamon Press 1984; Furan derivatives eg. AU579 693, U.S. Ser. No. 06/940649 or Advances in Heterocyclic Chemistry, Vol. 30, pages 167 et seq., 1982; thiazole derivatives, oxazole derivatives, isothiazole derivatives, thiadiazole derivatives and oxadiazole derivatives, eg. Comprehensive Heterocyclic Chemistry, A. R. Katritzky and C. W. Rees, Vol. 6, pages 166, 177, 235, 386, 425 et seq., Pergamon Press, 1984; imidazole derivatives, eg. Advances in Heterocyclic Chemistry, Vol. 27, pages 242 et seq., 1980; pyrazole derivatives, eg. Heteroaromatic Nitrogen Compounds, The Azoles, pages 31 et seq., Cambridge University Press, 1976; triazole derivatives, eg. Comprehensive Heterocyclic Chemistry, A. R. Katritzky and C. W. Rees, Vol. 5, pages 733 et seq., Pergamon Press, 1984; isoxazole derivatives eg. GB1560 711 and DE-A 2 754 832.

If the compounds of the formula I are basic, they can be converted into the addition salts of a physiologically tolerated acid. Examples of conventional physiologically tolerated organic and inorganic acids are hydrochloric acid, hydrobromic acid, phosphoric acid, sulfuric acid, maleic acid, fumaric acid, lactic acid, tartaric acid, adipic acid and benzoic acid. Others are to be found in Fortschritte der Arzneimittelforschung, Vol. 10, pages 224 et seq., Birkhäuser Verlag, Basel and Stuttgart, 1966.

The acid addition salts are usually obtained in a conventional way by mixing the free base or solutions thereof with the appropriate acid or solutions thereof in an organic solvent, for example in a lower alcohol such as methanol, ethanol or propanol, or an ether such as diethyl or methyl t-butyl ether,. Mixtures of the said solvents can also be used to improve crystallization. In addition, pharmaceutically acceptable aqueous solutions of acid addition compounds of the compounds I according to the invention can be prepared by dissolving the free bases in an aqueous acid solution.

The compounds of the formula I are inhibitors of monoamine oxidases (MAO) and therefore can be used for treating disorders of the central nervous system, especially neurodegenerative disorders and parkinsonism.

The MAO-inhibiting activity of the compounds according to the invention can be determined using standard methods. Thus, monoamine oxidases A and B were determined in dilute rat brain homogenate to which test substances in various concentrations and $^{14}$C-phenylethylamine or $^{14}$C-tryptamine in a concentration of 0.4 μmol/l were added. This mixture was incubated at 37° C. for 20 min.

The reaction was then stopped with 0.1 normal HCl, and the products were determined after extraction in a toluene scintillator (PPO+POPOP in toluene). The blank was determined on a similar mixture with an incubation time of 0 min.

The median inhibitory concentration (IC50) was calculated by linear regression after logit-log transformation from the values for the inhibition at the various concentrations relative to the control.

The activities found in this way for some compounds according to the invention are shown in the following table:

| Example | IC$_{50}$ [nmol/l] MAO A | MAO B | MAO A / MAO B |
|---|---|---|---|
| 1 | >10,000 | 1 | >10,000 |
| 2 | >10,000 | 3 | >3333 |
| 3 | >10,000 | 10 | >1000 |
| 4 | ≧10,000 | 2 | >5000 |
| 12 | ≧10,000 | 3 | >3333 |
| 13 | >10,000 | 3 | >3333 |
| 14 | >10,000 | 6 | >1667 |

The compounds according to the invention can be administered in a conventional way orally or parenterally (subcutaneously, intravenously, intramuscularly, intraperitoneally).

The dosage depends on the age, condition and weight of the patient and on the mode of administration. As a rule, the daily dose of active substance is about 10–1000 mg per patient and day on oral administration and about 1–200 mg per patient and day on parenteral administration.

The novel compounds can be used in conventional solid or liquid pharmaceutical forms, eg. as uncoated or (film-)coated tablets, capsules, powders, granules, suppositories, solutions or sprays. These are prepared in a conventional way. The active substances can for this purpose be processed with conventional pharmaceutical auxiliaries such as tablet binders, fillers, preservatives, tablet disintegrants, flow regulators, plasticizers, wetting agents, dispersants, emulsifiers, solvents, retarding agents, antioxidants and/or propellant gases (cf. H. Sucker et al.: Pharmazeutische Technologie, Thieme-Verlag, Stuttgart, 1978). The administration forms obtained in this way normally contain the active substance in a concentration of from 1 to 99% by weight.

EXAMPLES

General method of preparation 10 mmol of coumarin derivative of the formula II were stirred with 10 mmol (4.04 g) of Lawesson's reagent (2,4-bis(4-methoxyphenyl)-1,3-dithia-2,4-diphosphetane 2,4-disulfide) in 20 ml of toluene at 90° C. for 1–2.5 h. After cooling, the solvent was distilled off, the residue was taken up in DMF, and water was added.

The precipitate was filtered off with suction and the crude product was purified by recrystallization from methanol or by column chromatography (silica gel, methylene chloride).

The following was prepared by this method:

EXAMPLE 1

3,4-Dimethyl-7-(2-isopropyl-1,3,4-thiadiazol-5-ylmethoxy)-2-thiocoumarin
Yield: 98%
Melting point: 134°–135° C.

EXAMPLE 2

3,4-Dimethyl-7-(2-isopropylthiazol-4-ylmethoxy)-2-thiocoumarin
Yield: 66%
Melting point: 115° C.

EXAMPLE 3

3,4-Dimethyl-7-(2-methyl-1,3,4-oxadiazol-5-ylmethoxy)-2-thiocoumarin
Yield: 87%
Melting point: 187°–188° C.

EXAMPLE 4

3,4-Dimethyl-7-(2-n-propyl-1,3,4-thiadiazol-5-ylmethoxy)-2-thiocoumarin
Yield: 70%
Melting point: 95°–96° C.

EXAMPLE 5

3,4-Dimethyl-7-(1-methyl-5-isopropylpyrazol-3-ylmethoxy)-2-thiocoumarin
Yield: 52%
Melting point: 135°–136° C.

EXAMPLE 6

3,4-Dimethyl-7-(2-cyclopropyl-1,3,4-thiadiazol-5-ylmethoxy)-2-thiocoumarin
Yield: 76%
Melting point: 145°–146° C.

EXAMPLE 7

7-[3-(1-Methoxyethyl)-isoxazol-5-ylmethoxy]-3,4-dimethyl-2-thiocoumarin
Yield: 24%
Melting point: 91°–92° C.

EXAMPLE 8

3,4-Dimethyl-7-(3-n-propylisoxazol-5-ylmethoxy)-2-thiocoumarin
Yield: 84%
Melting point: 105°–106° C.

EXAMPLE 9

7-[3-(Tetrahydrofuran-3-yl)-isoxazol-5-ylmethoxy]-3,4-dimethyl-2-thiocoumarin
Yield: 23%
Melting point: 118°–119° C.

EXAMPLE 10 l 7-(2-Chlorothien-5-ylmethoxy)-3,4-dimethyl-2-thiocoumarin
Yield: 50%
Melting point: 176°–178° C.

EXAMPLE 11

7-Benzyloxy-2-thiocoumarin
Yield: 96%
Melting point: 176°–177° C.

EXAMPLE 12

7-(4-Isopropylbenzyloxy)-2-thiocoumarin
Yield: 75%
Melting point: 142°–143° C.

EXAMPLE 13

6-Chloro-3,4-dimethyl-7-(2-isopropyl-1,3,4-thiadiazol-5-ylmethoxy)-2-thiocoumarin
Yield: 84%
Melting point: 228°–229° C.

EXAMPLE 14

6-Chloro-3,4-dimethyl-7-(2-cyclopropyl-1,3,4-thiadiazol-5-ylmethoxy)-2-thiocoumarin
Yield: 40%
Melting point: 241°–242° C.

EXAMPLE 15

7-(2-Methyl-1,3,4-thiadiazol-5-ylmethoxy)-4-phenyl-2-thiocoumarin
Yield: 66%
Melting point: 187°–188° C.

EXAMPLE 16

7-(2-Methyl-1,3,4-thiadiazol-5-ylmethoxy)-3,4-tetramethylene-2-thiocoumarin
Yield: 41%
Melting point: 159°–160° C.

USE EXAMPLES

A) Tablets of the following formulation were made in a conventional tableting machine:
40 mg of substance of Example 1
120 mg of corn starch
13.50 mg of gelatin
45.00 mg of lactose
2.25 mg of Aerosil® (chemically pure, submicroscopically fine silica)
6.75 mg of potato starch (as 6% paste)
B) 20.00 mg of substance of Example 11
60.00 mg of core composition
60.00 mg of coating composition The core compositions comprises 9 parts of corn starch, 3 parts of lactose and 1 part of Luviskol® VA 64 (60:40 vinylpyrrolidone/vinyl acetate copolymer, cf. Pharm. Ind. 1962, 586). The coating composition comprises 5 parts of sucrose, 2 parts of corn starch, 2 parts of calcium carbonate and 1 part of talc. The coated tablets produced in this way are subsequently provided with an enteric coating.

We claim:
1. An arylalkoxythiocoumarin of the formula

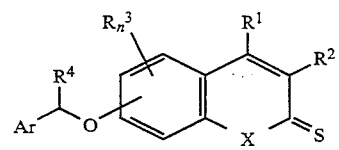

where
$R^1$ and $R^2$ are each, independently of one another, hydrogen, $C_1$–$C_5$-alkyl, trifluoromethyl, phenyl or halogen, or together are a $C_3$–$C_5$-alkylene chain, and X is oxygen or sulfur, $R^3$ is $C_1$-$C_5$-alkyl or halogen, n is an integer from 0 to 3, $R^4$ is hydrogen or $C_1$-$C_4$-alkyl and Ar is phenyl, which can be mono- or disubstituted by halogen, $C_1$-$C_6$-alkyl, $C_3$-$C_7$-cycloalkyl, $C_1$-$C_6$-alkoxy, nitro, cyano, trifluoromethyl or a combination of these substituents or is a heteroaromatic ring which has from one to three heteroatoms which can, independently of one another, be N, O or S, and which can be substituted by $C_1$-$C_6$-alkyl, $C_3$-$C_7$-cycloalkyl, $C_1$-$C_6$-alkoxy, $C_1$-$C_4$-alkoxy-substituted $C_1$-$C_6$-alkyl, 5–6-membered oxacycloalkyl, benzyl, $C_1$-$C_5$-alkoxycarbonyl, perfluoro-$C_1$-$C_2$-alkyl, phenyl or halogen.

2. An oral therapeutic composition which contains as active ingredient from 10 to 1000 mg, per dose, of a compound of the formula I as claimed in claim 1 in addition to conventional pharmaceutical auxiliaries.

3. An parenteral therapeutic composition which contains as active ingredient from 1 to 200 mg, per dose, of a compound of the formula I as claimed in claim 1 in addition to conventional pharmaceutical auxiliaries.

4. A pharmaceutical composition for inhibiting monoamineoxidase comprising:

an effective amount of an arylalkoxythiocoumarin of formula I in claim 1, and a pharmaceutically acceptable carrier or excipient.

* * * * *